United States Patent [19]
Hamm

[11] Patent Number: 5,949,929
[45] Date of Patent: Sep. 7, 1999

[54] ROTATABLY CONNECTING OPTICAL FIBERS

[75] Inventor: Mark A. Hamm, Lynnfield, Mass.

[73] Assignee: Boston Scientific Corporation, Natick, Mass.

[21] Appl. No.: 09/229,371

[22] Filed: Jan. 13, 1999

Related U.S. Application Data

[62] Division of application No. 08/758,146, Nov. 25, 1996, Pat. No. 5,872,879.

[51] Int. Cl.⁶ ..................................................... G02B 6/26
[52] U.S. Cl. .............................................................. 385/25
[58] Field of Search ............................... 385/24–25, 27, 385/31, 39, 53, 147

[56] References Cited

U.S. PATENT DOCUMENTS

| | | | |
|---|---|---|---|
| 4,398,791 | 8/1983 | Dorsey | 350/96.18 |
| 4,525,025 | 6/1985 | Hohmann et al. | 350/96.15 |
| 4,641,915 | 2/1987 | Asakawa et al. | 350/96.18 |
| 4,753,501 | 6/1988 | Battle | 385/22 |
| 4,772,093 | 9/1988 | Abele et al. | 350/96.25 |
| 4,815,812 | 3/1989 | Miller | 350/96.21 |
| 4,898,447 | 2/1990 | Kuhlmann | 350/96.2 |
| 4,909,589 | 3/1990 | Morris | 385/25 |

(List continued on next page.)

FOREIGN PATENT DOCUMENTS

| | | |
|---|---|---|
| 2 527 790 | 12/1983 | France . |
| WO 96/41225 | 12/1996 | WIPO . |
| WO 97/03374 | 1/1997 | WIPO . |
| WO 97/04341 | 2/1997 | WIPO . |
| WO 97/04342 | 2/1997 | WIPO . |
| WO 97/09646 | 3/1997 | WIPO . |
| WO 97/09647 | 3/1997 | WIPO . |

OTHER PUBLICATIONS

"Collimating and Focusing Lenses", Melles Griot, pp. 20–43 and 20–58 to 20–60. (No Date).

"Optical Fiber Connector in a Delivery System for Medical Applications", by M. Brenci, R. Falciai, V. Russo and A. Scheggi, Istituto Di Ricerca Sulle Onde Elettromagnetiche Del CNR, *Alta Frequenza*, Jul.–Aug. 1981, vol. L, N.4, pp. 223–224.

"Research on an Expanded Beam Single–Mode Fiber–Optic Connector" by H.M. Presby, A. Benner and N. Amitay, *Applied Optics*, vol. 27, No. 15, Aug. 1, 1988, pp. 3121–3122.

*Primary Examiner*—Akm E. Ullah
*Attorney, Agent, or Firm*—Testa, Hurwitz & Thibeault, LLP

[57] ABSTRACT

A connection includes an interventional medical device having a rotatable optical fiber, an assembly having a conduit for conveying a light beam to the rotatable fiber as well as a rotor and a fixed housing, and a coupling. A drive mechanism is attached to the rotor for continuously rotating the rotor. The coupling includes a rotatable portion attachable to a proximal end of the rotatable fiber and to the rotor so as to permit the rotatable fiber to rotate continuously with the rotor while the rotatable fiber remains in axial alignment with the light beam. The coupling also includes a stationary shield surrounding the rotatable portion. The stationary shield is attachable to the fixed housing so as to urge the rotatable portion and the rotor together. The proximal end of the rotatable portion of the coupling has a vee-shaped coupling surface that complements a distal end surface of the rotor. The rotor is at least partially hollow and includes a bearing that holds the light beam conduit in axial alignment with the rotatable fiber when the rotatable portion of the coupling engages the rotor. The rotatable fiber may be disengageable from the rotatable portion of the coupling when the stationary shield does not engage the fixed housing. The rotatable fiber may be surrounded by a sheath that is attachable to the stationary portion of the coupling. A fluid port connected to the stationary portion of the coupling enables introduction of fluid into the sheath and around the rotatable optical fiber.

19 Claims, 13 Drawing Sheets

U.S. PATENT DOCUMENTS

| | | | |
|---|---|---|---|
| 4,913,513 | 4/1990 | Kuromatsu et al. | 350/96.21 |
| 4,943,137 | 7/1990 | Speer | 350/96.18 |
| 5,039,193 | 8/1991 | Snow et al. | 385/25 |
| 5,109,859 | 5/1992 | Jenkins | 128/662.03 |
| 5,140,289 | 8/1992 | Andrieu et al. | 333/256 |
| 5,157,745 | 10/1992 | Ames | 385/26 |
| 5,354,993 | 10/1994 | Kedmi et al. | 250/551 |
| 5,371,814 | 12/1994 | Ames et al. | 385/25 |
| 5,436,988 | 7/1995 | Narendran | 385/26 |
| 5,450,509 | 9/1995 | Davis | 385/26 |
| 5,535,294 | 7/1996 | Kamuz et al. | 385/25 |
| 5,561,726 | 10/1996 | Yao | 385/11 |
| 5,621,830 | 4/1997 | Lucey et al. | 385/25 |
| 5,872,879 | 2/1999 | Hamm | 385/25 |

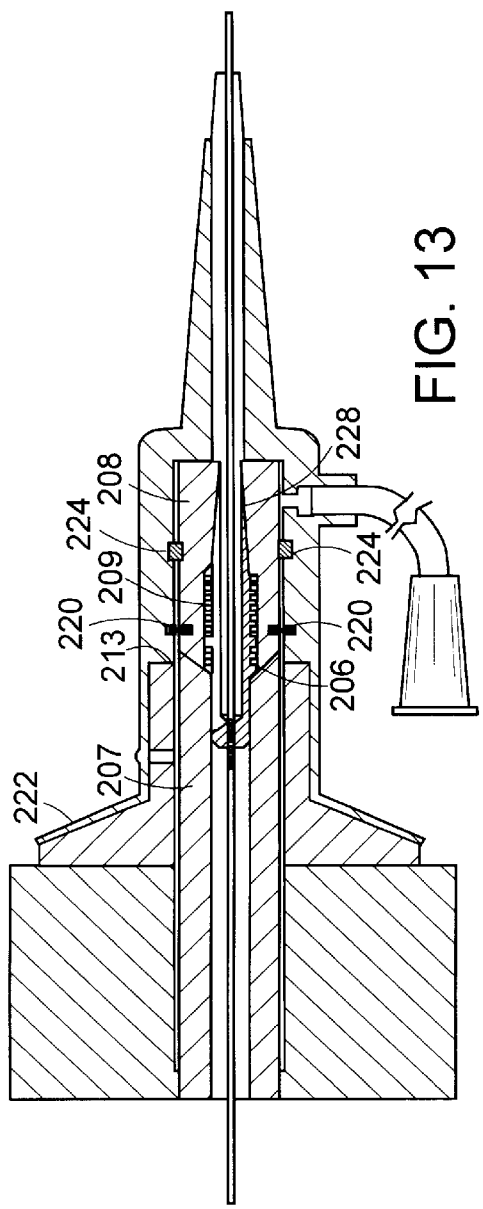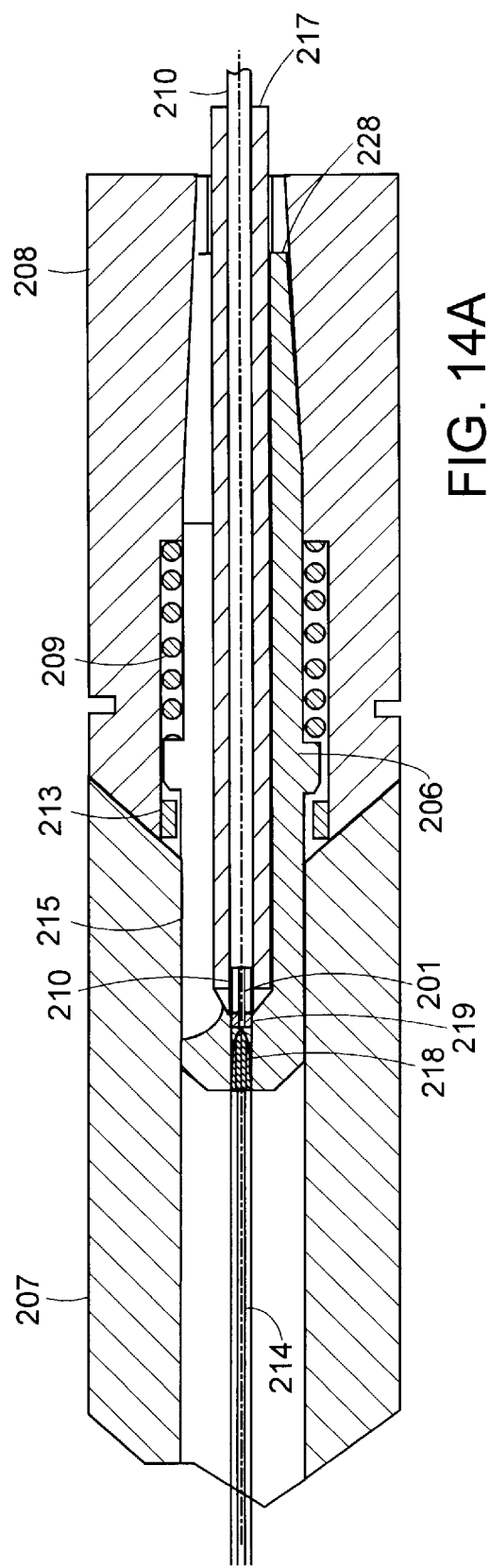

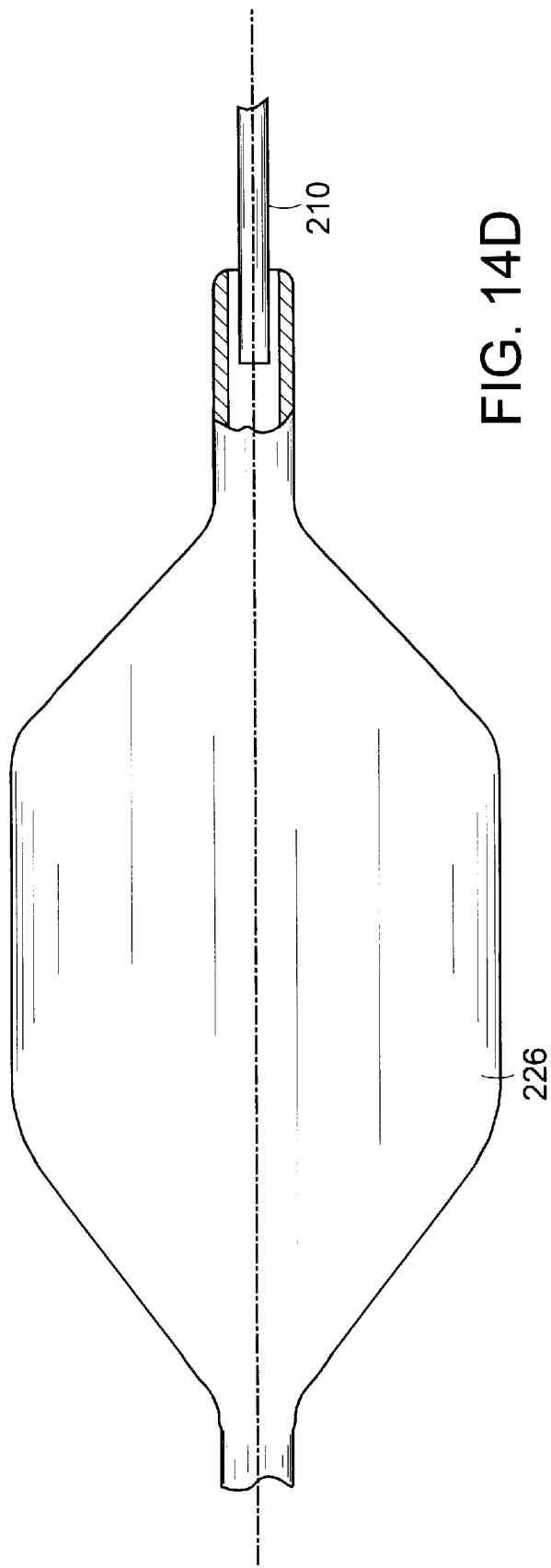

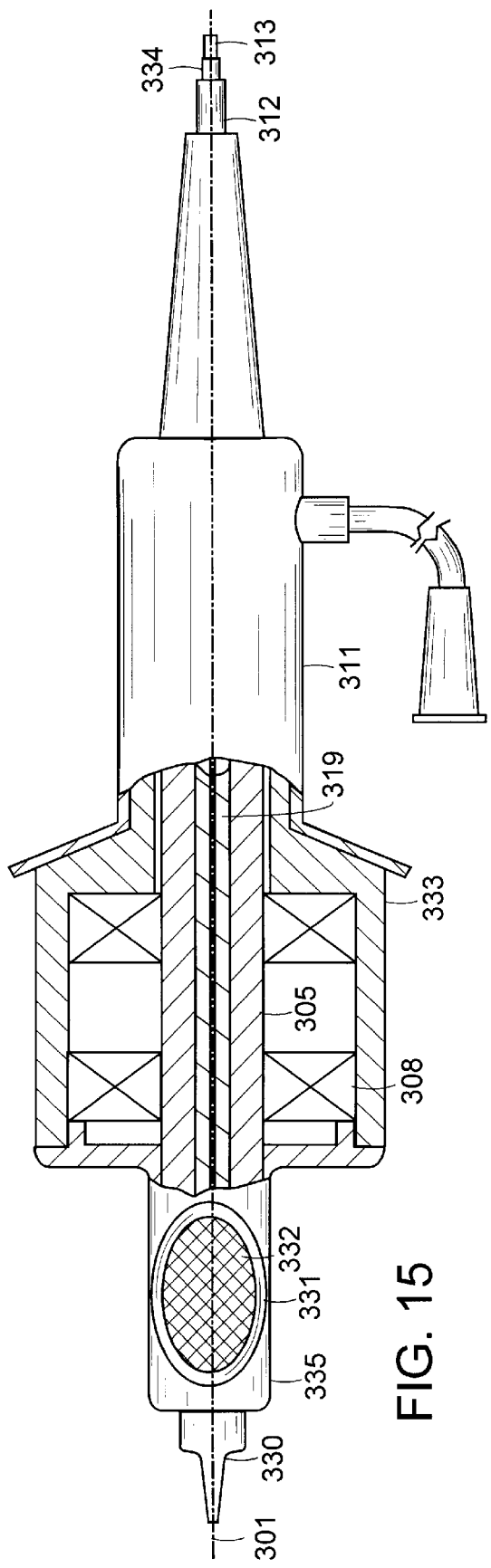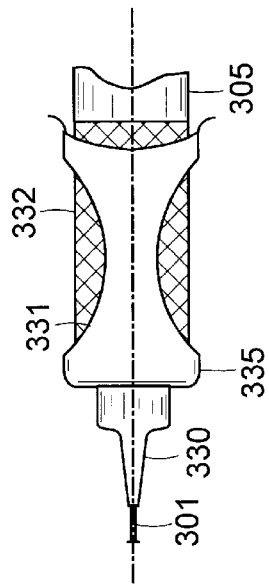

ROTATABLY CONNECTING OPTICAL FIBERS

This application is a divisional of application Ser. No. 08/758,146, filed Nov. 25, 1996 now U.S. Pat No. 5,872,879.

BACKGROUND OF THE INVENTION

This invention relates to connectors for connecting a rotatable optical fiber to a rotor shaft while maintaining the rotatable optical fiber in axial alignment with a stationary optical fiber.

Certain medical procedures such as in-vivo optical biopsy and optical coherence tomography (OCT) utilize diagnostic and interventional devices in conjunction with optical fibers that provide optical feedback to the clinician. The optical fibers are attached to an imaging console that displays an image or a processor that interprets data. Potential applications of such systems are stationary tissue spectroscopy of polyps and other mucosal tissues, linear scans of various portions of the human anatomy, and cross-sectional images of tubular vessels such as arteries, the gastrointestinal tract, urological structures, the biliary tree, and neurological vessels.

Procedures such as tissue spectroscopy typically utilize an endoscope, cystoscope, colonoscope, or sigmoidoscope for direct visual feedback. The scope helps direct a biopsy device to a site of interest, such as a polyp or dysplastic or cancerous tissue, and also provides a working channel for the biopsy device, a light source, and an optical path for visual guidance. Other procedures involving optical feedback use trocars for direct access to some parts of the anatomy, such as the breast for breast biopsies, or other areas inaccessible through an orifice.

SUMMARY OF THE INVENTION

One aspect of the invention features a connection system that includes an interventional medical device having a rotatable optical fiber, an assembly having a conduit for conveying a light beam to the rotatable fiber, and a coupling. The coupling has a rotatable portion attachable to a proximal end of the rotatable fiber, and a stationary portion attachable to the assembly that includes the light beam conduit so as to permit the rotatable fiber to rotate while its proximal end remains in axial alignment with the light beam.

According to another aspect of the invention the assembly having the light beam conduit includes a rotor and a fixed housing. A drive mechanism is attached to the rotor for continuously rotating the rotor. The stationary portion of the coupling is attachable to the fixed housing, and the rotatable portion is attachable to the rotor so as to permit the rotatable fiber to rotate continuously with the rotor while the rotatable fiber remains in axial alignment with the light beam.

According to another aspect of the invention the proximal end of the rotatable portion of the coupling has a vee-shaped coupling surface that complements a distal end surface of the rotor. This aspect of the invention helps to ensure that the rotary and stationary optical fibers are properly aligned so as to minimize insertion loss and return loss (Fresnel loss) by ensuring that any angular, lateral, or axial misalignment between the optical fibers is minimized.

According to another aspect of the invention the stationary portion of the coupling is a stationary shield surrounding the rotatable portion. The stationary shield is attachable to the fixed housing so as to urge the rotatable portion and the rotor together. In certain embodiments the stationary shield can automatically interlock with the stationary portion of the rotor assembly. Thus, the stationary shield can be fitted onto the stationary portion of the rotor assembly with the use of a single, sterile hand holding the stationary shield. This helps to maintain a sterile field around the patient and provides ease of use during medical procedures. Thus, the invention provides a low-cost (possible single-use), reliable, ergonomic rotary fiber-optic connector, useful in the field of percutaneous diagnostic and interventional medicine, that can be attached to a non-sterile drive motor or imaging console with one hand.

According to another aspect of the invention the rotatable fiber is disengageable from the rotatable portion of the coupling when the stationary portion of the coupling does not engage the fixed housing. Thus, the rotatable fiber and an optional catheter sheath surrounding the rotatable fiber (which may have an outside diameter of about 0.50 mm or less) can serve as a guidewire so that a catheter with a guidewire lumen or monorail tip can be passed over it.

Another aspect of the invention features a sheath surrounding the rotatable fiber and attachable to the stationary portion of the coupling, and a fluid port connected to the stationary portion of the coupling that enables introduction of fluid into the sheath and around the rotatable optical fiber.

According to another aspect of the invention the rotor is at least partially hollow and includes a bearing that holds the light beam conduit in axial alignment with the rotatable fiber when the rotatable portion of the coupling engages the rotor. Because the rotor shaft is hollow and the stationary optical fiber has a distal end portion positioned within the hollow rotor shaft, the distal end portion of the stationary optical fibers and the proximal end portion of the rotatable optical fiber can be located in the vicinity of the distal end surface of the rotor shaft and the proximal end surface of the rotatable coupling. This provides a simple configuration for quickly and easily connecting the rotatable coupling with the rotor shaft while maintaining the rotatable optical fiber in axial alignment with the stationary optical fiber. The configuration also protects the end surfaces of the optical fibers (or the lenses to which the end surfaces are connected) from damage and contaminants that would interfere with the signal.

Numerous additional objects and advantages of the invention will become apparent from the detailed description and the drawings.

BRIEF DESCRIPTION OF THE DRAWINGS

FIG. 13 is a cross-sectional view of a fiber-optic rotary connector and a motor assembly similar to the connector and motor assembly of FIG. 9 but including a rotatable GRIN rod lens.

FIGS. 14A–14D are detailed cross-sectional views of a the rotary connector of FIG. 13 showing the steps of disengaging the proximal end of the guidewire from the rotatable ferrule in the rotary connector and inserting a catheter over the proximal end of the guidewire.

FIG. 15 is a side view, partially in cross section, of a fiber-optic rotary connector attached to a rotor assembly having a manually rotatable rotor shaft.

FIG. 16 is a top view of a portion of the rotor assembly shown in FIG. 15.

DETAILED DESCRIPTION

Figure 1:
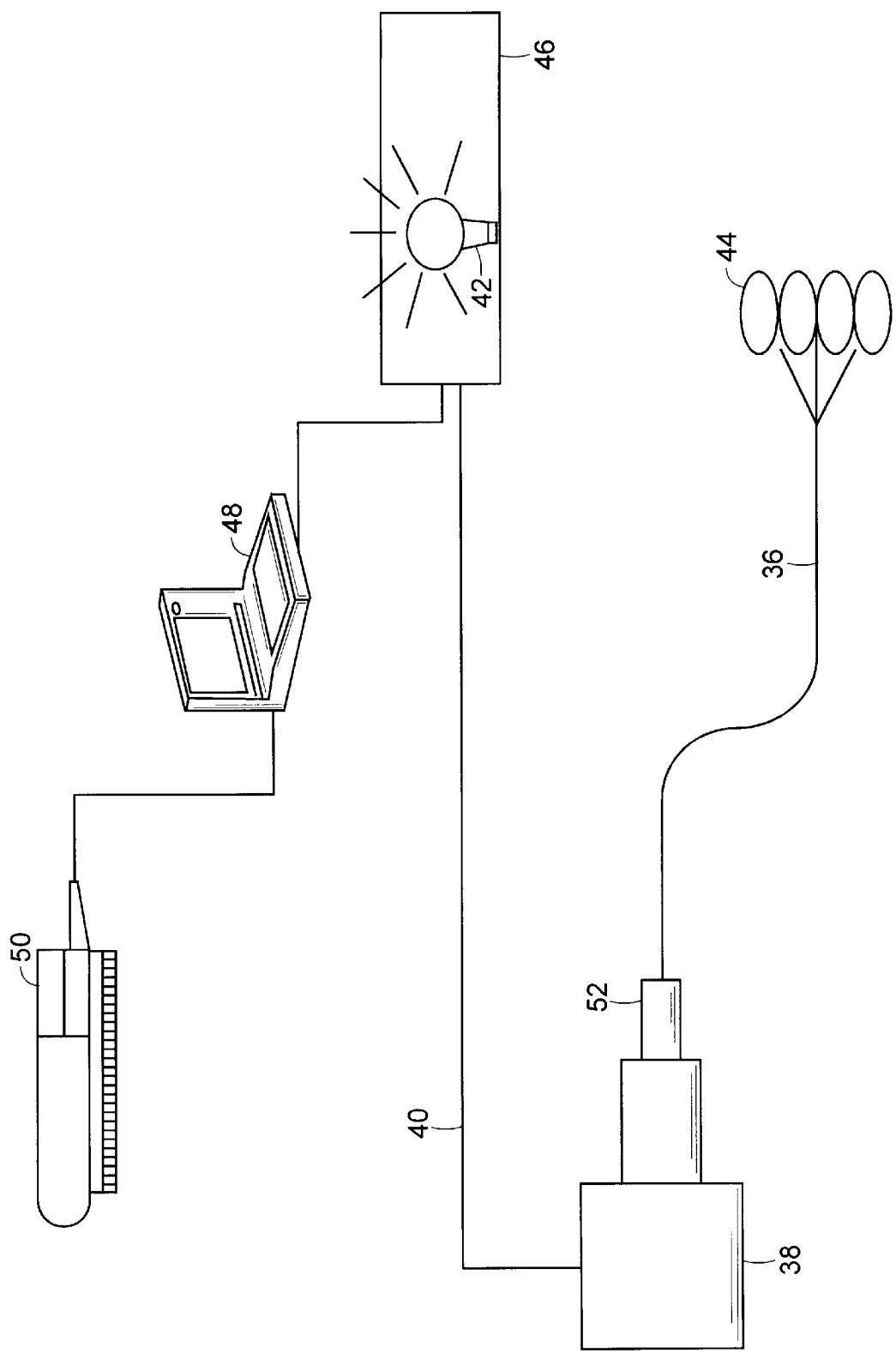
FIG. 1 is a block diagram of an optical catheter system.

With reference to FIG. 1, the rotary optical connection systems described in detail below may be used to attach a fiber-optic imaging catheter or guidewire or a spectroscopy catheter or guidewire 36 to a drive unit 38 and to an extension optics cable 40, by means of fiber-optic rotary connector 52. A light source 42 provides light for illuminating tissue 44 through catheter or guidewire 36. Catheter or guidewire 36 also conveys reflected or fluorescent light from tissue 44 back to a spectrometer or imaging system 46. If catheter or guidewire 36 is used for tissue spectroscopy, a personal computer 48 can analyze the spectroscopic data to determine the probability of a malignancy and can print out the data and analysis on a printer 50.

Figure 2:
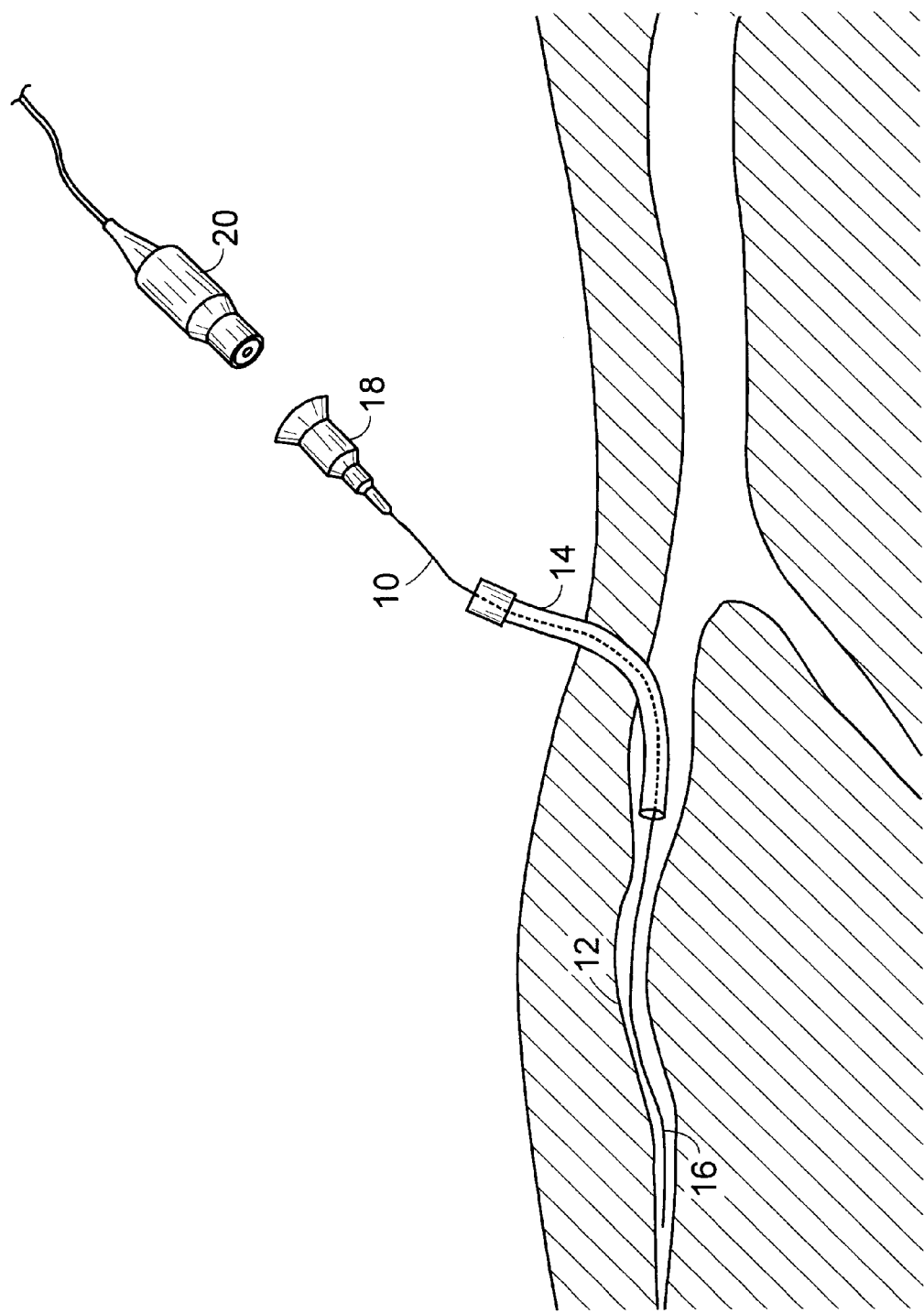
FIG. 2 is a drawing of an optical catheter in use within a patient's body and showing a fiber-optic rotary connector detached from a fiber-optic motor assembly.
Figure 3:
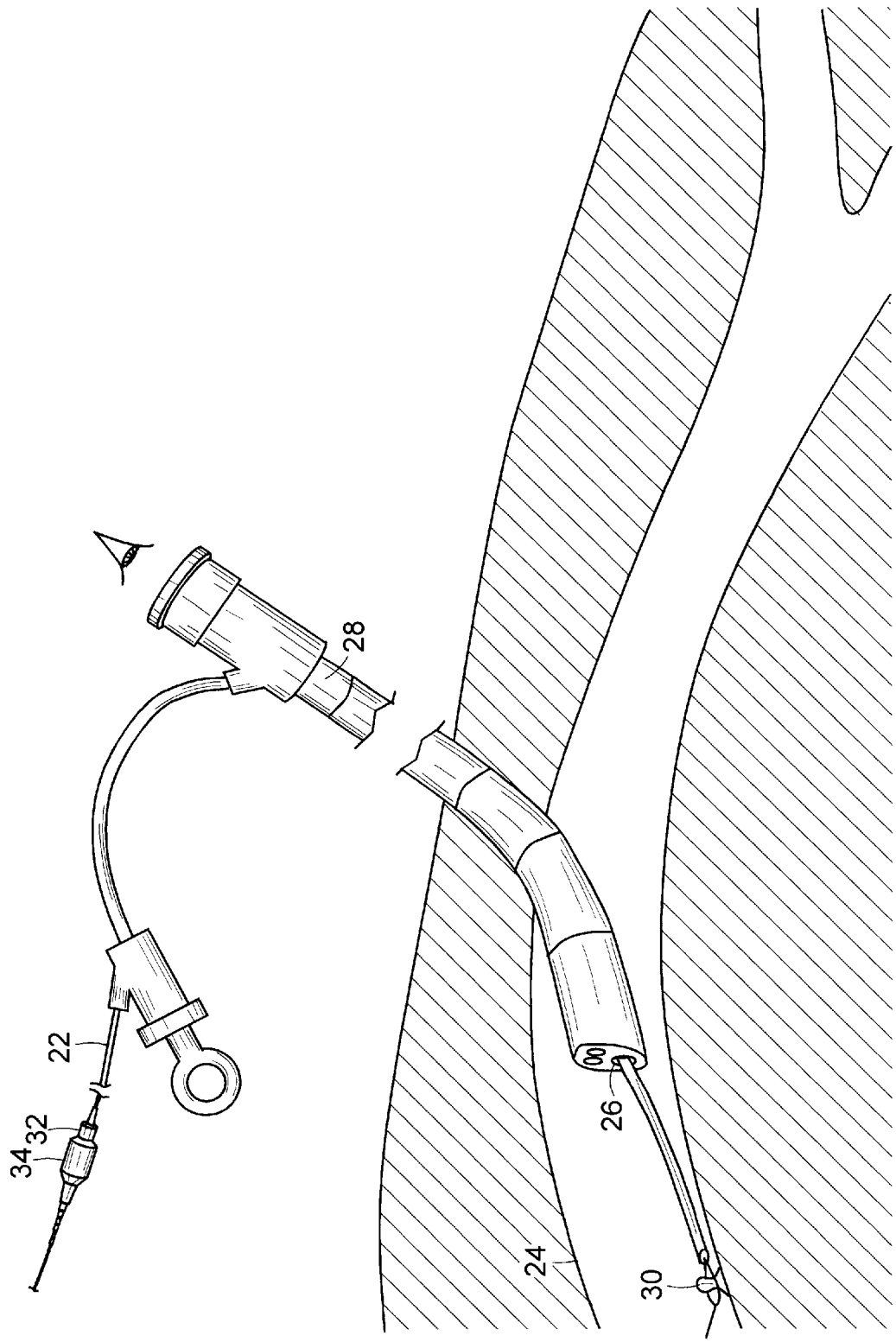
FIG. 3 is a drawing of an tissue spectroscopy snare catheter inserted into a patient's body through an endoscope and showing a fiber-optic rotary connector attached to a fiber-optic motor assembly.

FIG. 2 shows an example of an optical coherence tomography catheter 10 introduced into a lumen 12 of a patient's body through an introducer catheter 14 so as to image a region of interest 16. Fiber-optic rotary connector 18 is shown detached from fiber-optic motor assembly 20. FIG. 3 shows an example of a tissue spectroscopy snare catheter 22 inserted into a lumen 24 of a patient's body through a working channel 26 of an endoscope 28 so as to diagnose a polyp 30 through the use of tissue spectroscopy and possibly to remove the polyp, as is described in detail in U.S. patent application Ser. No. 08/679,425, filed Jul. 8, 1996 by Doug Daniels and entitled "Diagnosing and Performing Interventional Procedures in Vivo" the entire disclosure of which is hereby incorporated herein by reference. Fiber-optic rotary connector 32 is shown attached to a fiber-optic motor assembly or manually rotated connector 34.

Figure 4:
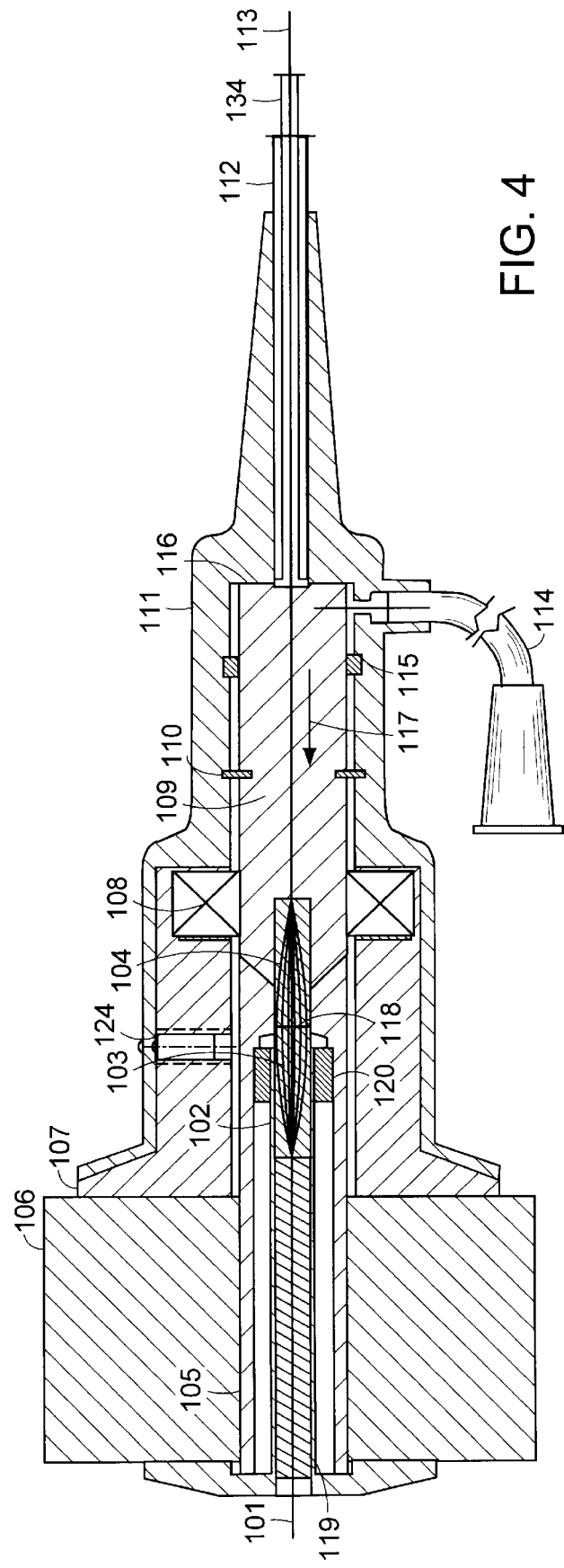
FIG. 4 is a cross-sectional drawing of a fiber-optic rotary connector attached to a fiber-optic motor assembly.

FIG. 4 illustrates a motor assembly and fiber-optic rotary connector in accordance with the invention that can be used in connection with optical coherence tomography catheters and spectroscopy catheters of the type illustrated in FIGS. 2 and 3. A motor assembly that includes motor 106, stationary nose piece 107, and a rotor shaft 105 is removably connected with a fiber-optic connector that includes rotatable vee-shaped coupling 109 and stationary sterile shield 111. Vee-shaped coupling 109 and sterile shield 111 may be disposable.

Stator fiber 101, which may be a single-mode optical fiber, a multi-mode fiber, or an optical fiber bundle, is aligned with stator GRIN (GRadient INdex of refraction) rod lens 102, available as, for example, Melles Griot product number #06-LGS-112. Both stator fiber 101 and stator GRIN rod lens 102 are held inside stationary tube 119, which is in turn held within rotatable stainless-steel rotor shaft 105 by means of a bearing or bushing 120 that permits rotor shaft 105 to rotate relative to stator fiber 101 and stator GRIN rod lens 102 at speeds up to about 5000 RPM. Stator fiber 101 and stator GRIN rod lens 102 are held in close proximity with rotor GRIN rod lens 104 and rotatable fiber 113 by means of a rotor vee-shaped coupling 109 that rotates inside stationary sterile shield 111. Vee-shaped coupling 109 is made of a biocompatible injection moldable or machined rigid material such as nylon, polycarbonate, plexiglass, PEBAX, aluminum, brass, etc., and stationary shield 111 is made of an biocompatible injection-molded elastomer such as polyethylene, polyolefin, or PEBAX, and is ETO, gamma, or EB sterilizable (preferably all three). The distal end of the stationary shield functions as a strain relief for stationary catheter sheath 112. Catheter sheath 112 may be manufactured of an inexpensive, biocompatible material such as polypropylene, polystyrene, polyethylene, nylon, PEBAX, or PET. Rotatable fiber 113 is contained with a rotatable driveshaft 134 inside stationary catheter sheath 112 (for purposes of visual clarity the distal ends of catheter sheath 112 and rotatable driveshaft 134 are shown cut away in FIG. 4). Rotatable driveshaft 134 ensures uniform rotation at the distal tip of rotatable fiber 113.

In one particular embodiment stator fiber 101 and rotatable fiber 113 are multiple-fiber bundles having a diameter of approximately 50 $\mu$m (0.0020 inches). The use of multiple-fiber bundles provides high flexibility and throughput. The fibers may be silica or plastic methylmethacrylate fibers with a numerical aperture of about 0.2–0.8. Single-mode optical fiber core sizes typically range from 70 $\mu$m (0.0025 inches) in diameter to 110 $\mu$m (0.0045 inches) in diameter, with the outer diameter of the fiber typically being about 125 $\mu$m (0.0050 inches). Single-mode optical fibers, which are generally used, for example, in optical coherence tomography, generally require more demanding and precise alignment than multi-mode optical fibers.

A stainless steel retaining spring clip 110 holds floating vee-shaped coupling 109 inside stationary sterile shield 111, and curved low-friction felt-fiber or TEFLON or Belleville washer 116 located between polished surfaces of vee-shaped coupling 109 and stationary shield 111 applies a small force (indicated by arrow 117) to keep rotor GRIN rod lens 104 and stator grin rod lens 102 in close proximity with each other during rotation. The force also keeps rotor shaft 105 and rotor vee-shaped coupling 109 in contact with each other during rotation. This contact maintains the proper gap 118 between stator GRIN rod lens 102 and rotor GRIN rod lens 104 to minimize light loss. An index of refraction matching gel could be used in gap 118. A bearing 108 is positioned between stationary, molded nose piece 107 and rotor vee-shaped coupling 109. Stationary nose piece 107 may be made of rigid, injection-molded polymer such as polycarbonate or from machined metal.

In one embodiment there is an interference fit between stationary shield 111 and the stationary nose piece 107 that automatically interlocks stationary shield 111 and stationary nose piece 107 when stationary shield 111 is slidably inserted over stationary nose piece 107. In other embodiments stationary shield 111 and stationary nose piece 107 include interlocking elements that engage each other to automatically interlock stationary shield 111 and stationary nose piece 107. For example, a ball plunger 124, or alternatively a spring plunger, may be provided between stationary shield 111 and nose piece 107. The ball plunger or spring creates an audible "click" when stationary shield 111 is properly interlocked with nose piece 107.

Luer adapter sidearm 114 is used with a conventional syringe to introduce fluid into the central lumen of catheter sheath 112 around rotor fiber 113, or into a separate lumen disposed within catheter sheath 112 alongside the optics lumen. Luer adapter sidearm 114 allows a slow drip or a strong flush to rinse away clots or other contaminants from a distal lens (not shown) at the distal end of rotor fiber 113 to facilitate cleaning of the lens. Also, an optically clear liquid such as saline solution can be injected into a vessel or area of interest through luer adapter sidearm 114. Alternatively, a coupling medium or a drug may be introduced through the luer adapter sidearm. O-ring 115, made of soft silicone, rubber or TEFLON, provides a seal between the polished surfaces of vee-shaped coupling 109 and stationary shield 111 to prevent fluid from passing into motor 106.

Figure 5:
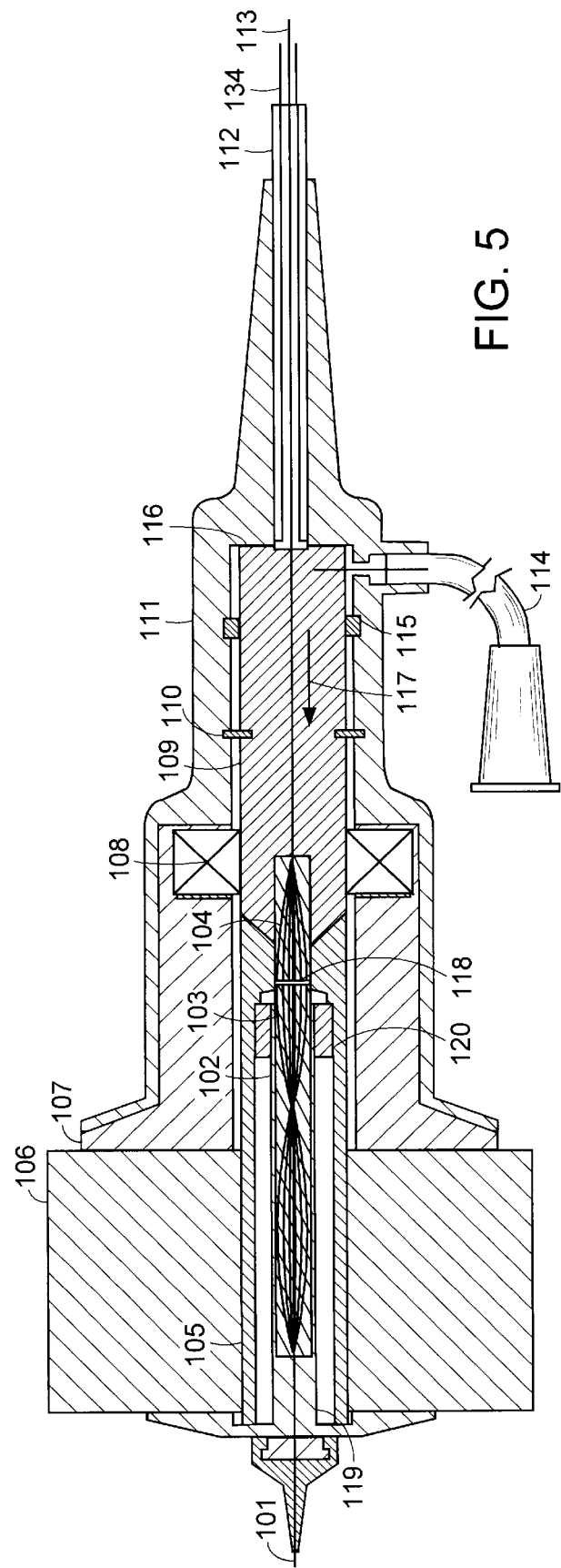
FIG. 5 is a cross-sectional drawing of a fiber-optic rotary connector attached to a fiber-optic motor assembly, the motor assembly including a stationary GRIN lens longer than the stationary GRIN lens shown in FIG. 4.

In FIG. 5, a GRIN rod lens 102 that is longer than the one shown in FIG. 4 extends through rotor shaft 105. The nature of GRIN rod lens 102 allows custom geometries that yield various desired results. In the case of FIG. 5, for example, GRIN lens 102 accepts light emanating from stator optical fiber 101, then bends the light into a sinusoidal path 103 through exactly 1 and ½ cycles, so that when the light exits the distal end of lens 102 it is collimated. In FIG. 4, in which the length of GRIN lens 102 is minimized, GRIN lens 102 bends the light into a sinusoidal path 103 through exactly ½ cycle. The collimated light that enters rotor lens 104 is then focused into rotor optical fiber 113 with minimized losses. By positioning rotor GRIN rod lens 104 within 0.001–0.005 inches from the matching distal face of stator lens 102 of FIG. 4 or FIG. 5, light loss is minimized. The use of GRIN rod lenses 102 and 104 reduces the need for precise alignment of optical fibers 101 and 113. This is especially important if the optical fibers are single-mode fibers. GRIN rod lenses 102 and 104 may be made of silica having fluoride-doped outer layers. GRIN rod lens 104 may be disposable along with vee-shaped coupling 109 and stationary shield 111. A detailed description of GRIN rod lenses can be found in U.S. Pat. No. 4,641,915.

Figure 6:
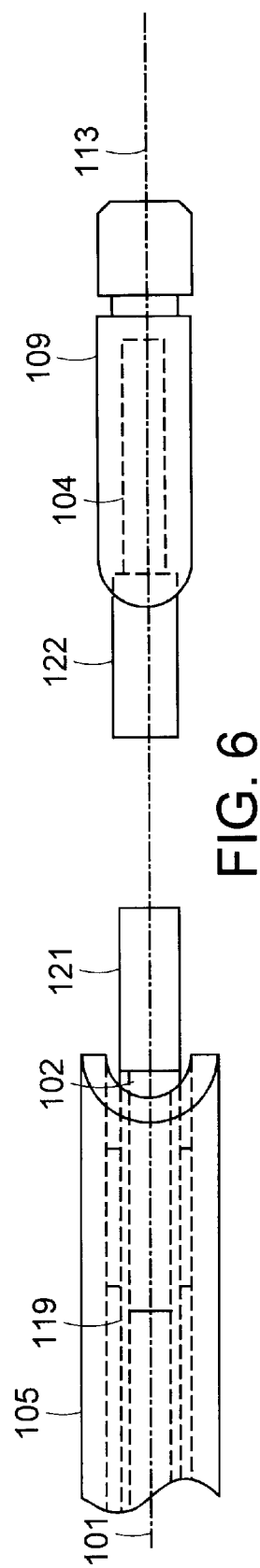
FIG. 6 is a top view of a motor coupling and a ferrule coupling, showing the use of a tool that fits the stationary and rotatable GRIN lenses within the motor coupling and ferrule coupling.
Figure 7:
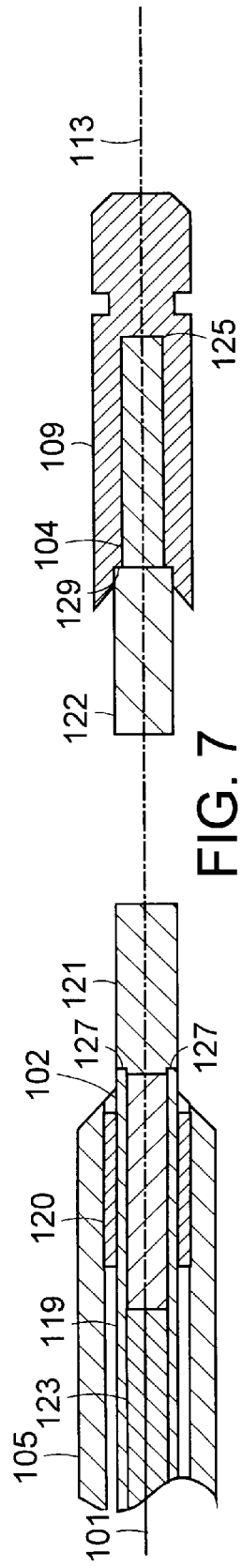
FIG. 7 is a cross-sectional side view of the motor coupling and ferrule coupling of FIG. 6.
Figure 8:
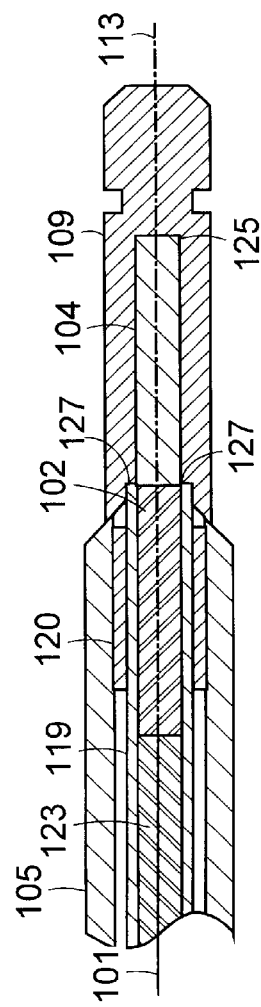
FIG. 8 is a cross-sectional side view of the motor coupling and ferrule coupling of FIG. 6 in engagement with each other.

FIGS. 6–8 show one particular construction of a rotor shaft 105 and vee-shaped coupling 109 (note that the elements shown in FIGS. 6–8 have somewhat different dimensions and shapes than the corresponding elements shown in FIGS. 4 and 5). Rod-like tool 121 is used to insert GRIN lens 102 into tube 119, and rod-like tool 122 is used to insert GRIN 104 into vee-shaped coupling 109. An index-matching ultraviolet-cured epoxy fills the slight gap 125 between GRIN lens 102 and spacer 123 and the slight gap between GRIN lens 104 and vee-shaped coupling 109 at the end of optical fiber 113. The distal end surface 127 of tube 119 acts as a stop that engages a complementary proximal end surface of vee-shaped coupling 109 as is shown in FIG. 8. Rod-like tool 121 sets the surface of GRIN lens 102 about 0.0010 inches from the distal end surface of tube 119, and rod-like tool 122 sets the surface of GRIN lens 104 flush with the C-bore 129 of vee-shaped coupling 109. When vee-shaped coupling 109 is mated with rotor shaft 105, tube 119 bottoms into the counterbore in vee-shaped coupling 109, leaving a 0.0010-inch gap between the GRIN lenses. The male and female vee shapes of vee-shaped coupling 109 and rotor shaft 105 mate with a small gap of about 0.0030 inches clearance to provide a positive drive system without binding or overtravel.

Figure 9:
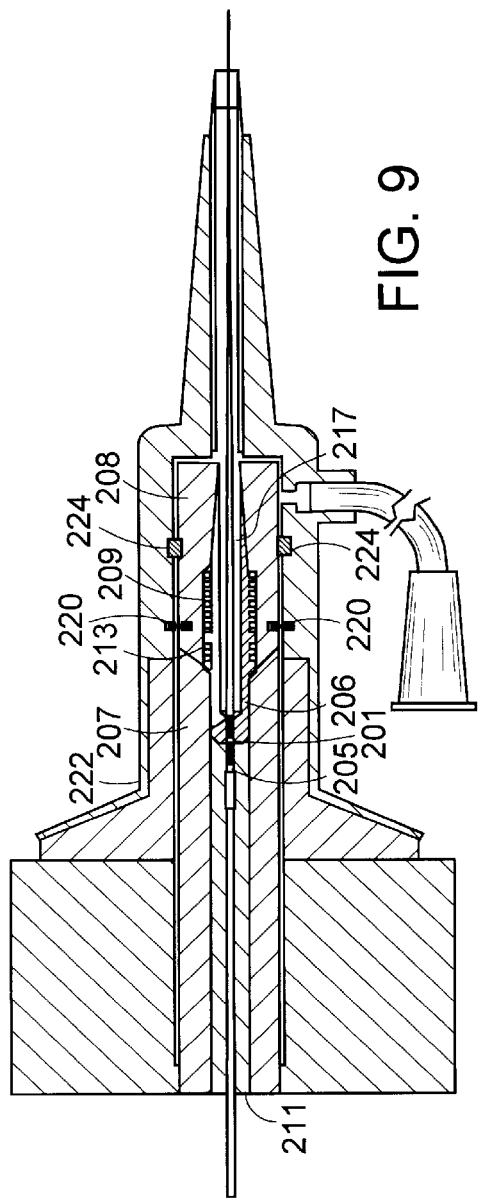
FIG. 9 is a cross-sectional view of a fiber-optic rotary connector attached to a fiber-optic motor assembly, in which the proximal end of a guidewire having a rotatable fiber is disengageable from a rotatable ferrule in the rotary connector.
Figure 10:
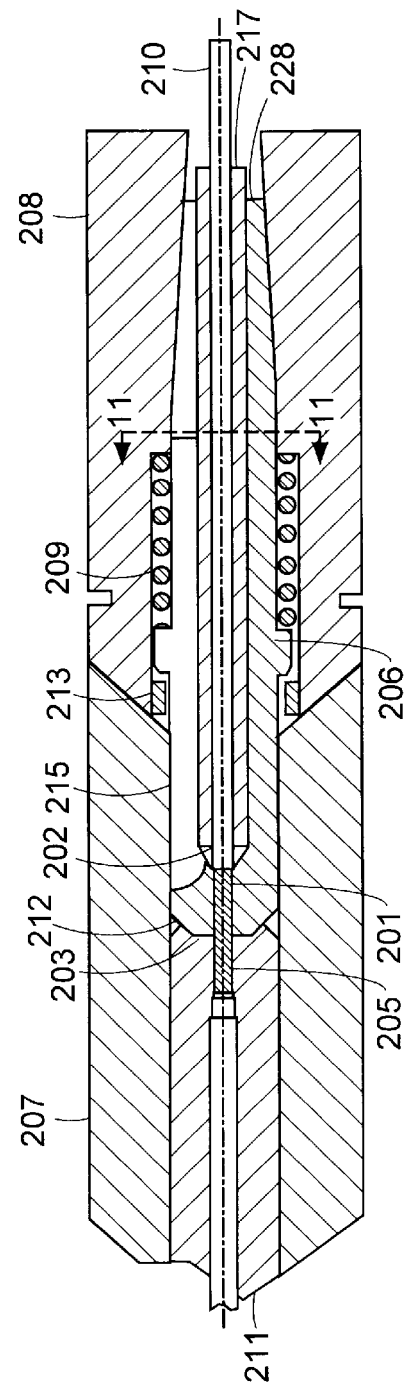
FIG. 10 is a detailed cross-sectional view of a portion of the rotary connector and a portion of the motor assembly shown in FIG. 9.

FIGS. 9 and 10 show a motor assembly and fiber-optic connector similar to those disclosed in FIGS. 4 and 5 except that rotor fiber optic core 201 and its metallic or plastic sleeve or sheath 210 form an optical guidewire that can be disengaged from a vee-shaped coupling 208, so that a catheter with a guidewire lumen or monorail tip can be passed over the optical guidewire. Rotor ferrule 206 and stator ferrule 211 align fiber optic cores 201 and 205, both in terms of lateral offset and angular alignment, thereby reducing optical loss at a butt joint 203 between the two fiber optic cores.

Vee-shaped coupling 208 attaches the optical guidewire to rotor shaft 207 in a manner similar to FIGS. 4 and 5 above. The embodiment of FIGS. 9 and 10 is different from the embodiments of FIGS. 4 and 5, however, in that the medical guidewire can be detached from vee-shaped coupling 208 and ferrule 206. The proximal end of the optical guidewire has an outer diameter of less than 0.0180 inches, which is substantially the same as that of the remainder of the guidewire.

Figure 11:
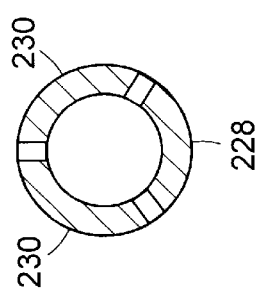
FIG. 11 is a cross-sectional drawing of the rotatable ferrule shown in FIG. 10, taken along line 11—11.

The proximal end of the guidewire is insertable into rotor ferrule 206, which has three fingers 228, 230, and 232 as shown in FIG. 11 (one finger 228, is shown in cross-section in FIG. 10). Fingers 228, 230, and 232 clamp onto a centering and gripping tube 217 by means of collet closing action. This collet closing action of rotor ferrule 206 occurs as the rotor ferrule is inserted into the central bore 215 of rotor shaft 207 and engages the end of stator ferrule 211 (i.e., when the rotary connector is engaged with the motor assembly). When this happens, the internal taper of vee-shaped coupling 208 closes rotor ferrule 206 onto the centering and gripping tube 217, which is made of a soft, supple material such as silicone rubber or PEBAX. This gripping force holds sleeve or sheath 210 of the stiff guidewire concentric with stator fiber optic core 205, and thus sleeve or sheath 210 helps attain the proper axial and angular alignment of rotor fiber optic core 201 and stator fiber optic core 205. The distal end surface of stator ferrule 211 includes a circumferential ridge 212 that engages the proximal end surface of rotor ferrule 206 to ensure that the rotor and stator optical fibers are in lateral and angular alignment with each other.

Retainer ring 213 retains rotor ferrule 206 inside vee-shaped coupling 208. A compression spring 209 pushes rotor ferrule 206 toward stator ferrule 211 to force the two ferrules to engage each other, thereby maintaining the proper gap between the rotor and stator optical fibers 201 and 205. When vee-shaped coupling 208 is detached from the motor assembly, compression spring 209 pushes rotor ferrule 206 all the way toward retainer ring 213, thereby resulting in collet opening action of rotor ferrule 206. This enables the guidewire to be detached from the motor and stationary optical fiber 201 and used as an ordinary guidewire without a bulky connector.

A stainless steel retaining spring clip 220 holds floating vee-shaped coupling 208 inside stationary sterile shield 222.

Sterile shield 222 slides along the guidewire as it is removed from rotor ferrule 206 and vee-shaped coupling 208. O-ring 224 provides a seal between the polished surfaces of vee-shaped coupling 208 and stationary shield 222 to prevent fluid from passing into the motor.

Figure 12:
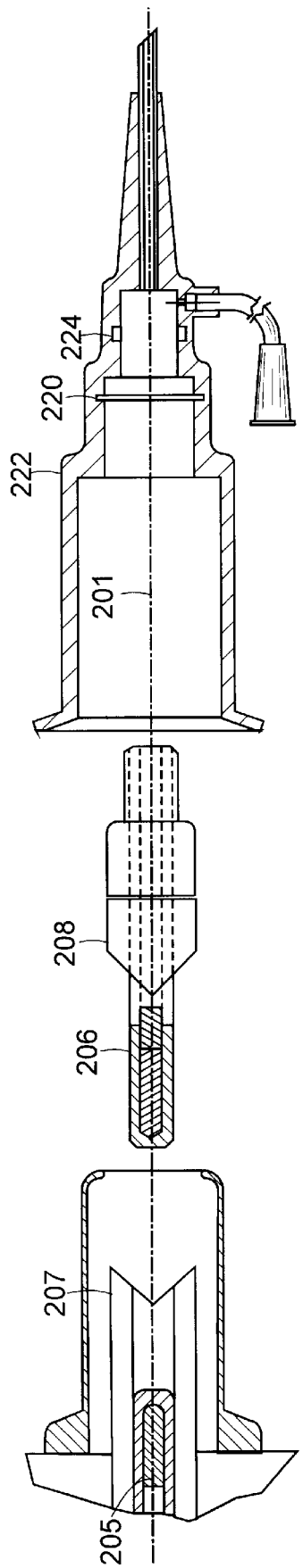
FIG. 12 is an exploded view, partially in cross-section, of another rotary connector and a portion of a motor assembly, in which the proximal end of a guidewire having a rotatable fiber is disengageable from a rotatable ferrule in the rotary connector.

FIG. 12 shows an exploded view of another rotary connector and a portion of a motor assembly similar to the rotary connector and motor assembly of FIGS. 9 and 10 but having slightly different dimensions and shapes of rotor ferrule 206, vee-shaped coupling 208, and stationary shield 222.

FIGS. 13 and 14A–D show a motor assembly and fiber-optic connector similar to those disclosed in FIGS. 9 and 10 except that the optical guidewire includes a rotor GRIN rod lens 218 having an outer diameter of about 0.0150 inches. The rotor GRIN rod lens reduces the need for high machine tolerances in the components of the rotary connector and the motor assembly. The rotor GRIN rod lens 218 in the guidewire receives a collimated light beam 214 and focuses it into rotor fiber optic core 201. This configuration allows the optical fiber to receive a collimated light beam 214 generated by any suitable collimated light source or any means of generating a collimated light beam, such as a stator GRIN rod lens, a laser, a laser diode, etc. If a stator GRIN rod lens is used to generate the collimated light beam, the stator GRIN rod lens may be located at the proximal end of the motor assembly, such that the stator GRIN rod lens and the rotor GRIN rod lens 218 are separated by a relatively large gap to simplify the process of mating the rotary connector and the motor assembly. The stator GRIN rod lens may be mounted either on the same axis as the rotor GRIN rod lens, or it may be mounted normal to the axis of the rotor GRIN rod lens provided that a mirror or beamsplitter is used to direct the collimated light beam onto the axis of the rotor GRIN rod lens 218.

Rotor GRIN rod lens 218 is mounted at the proximal end of the optical guidewire in a process that optimizes the fiber-to-lens interface and throughput. In particular, the rotor GRIN rod lens is mounted concentrically with rotor optic fiber core 201 via a doughnut-shaped alignment disk 219 using ultraviolet-curable epoxy. Then rotor fiber optic core 201 is inserted into guidewire sleeve or sheath 210.

Figure 14B:
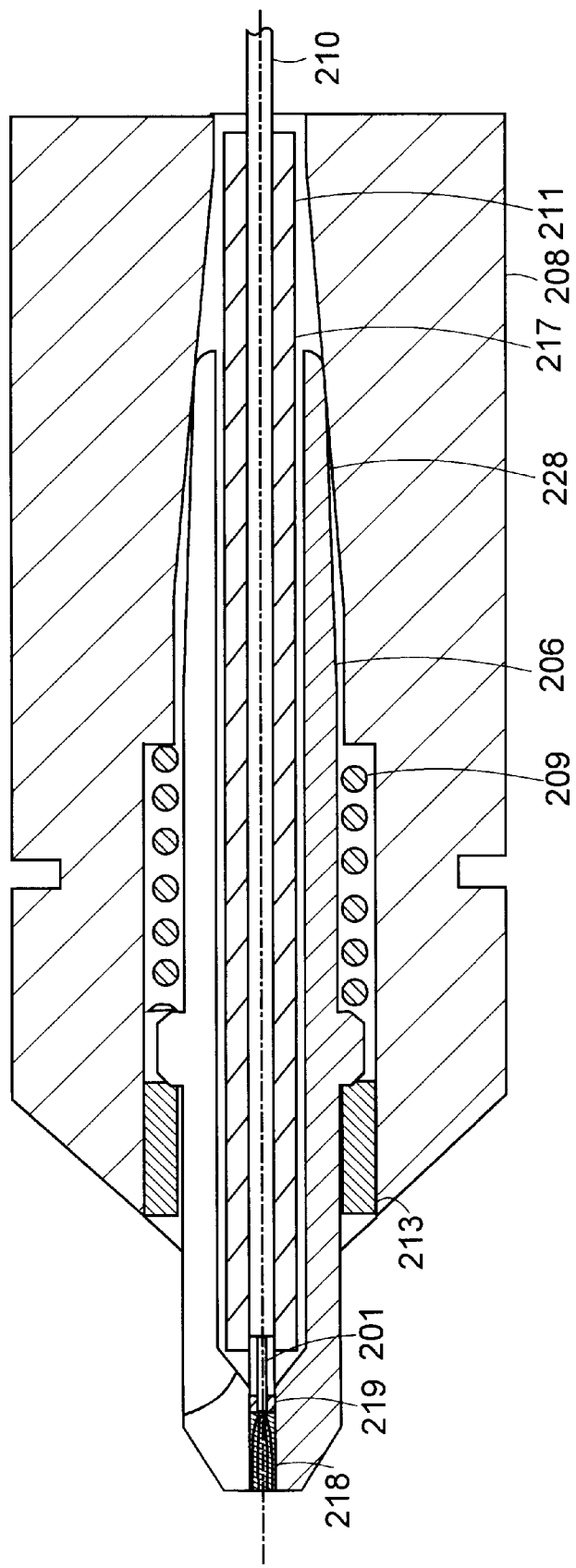
Figure 14C:
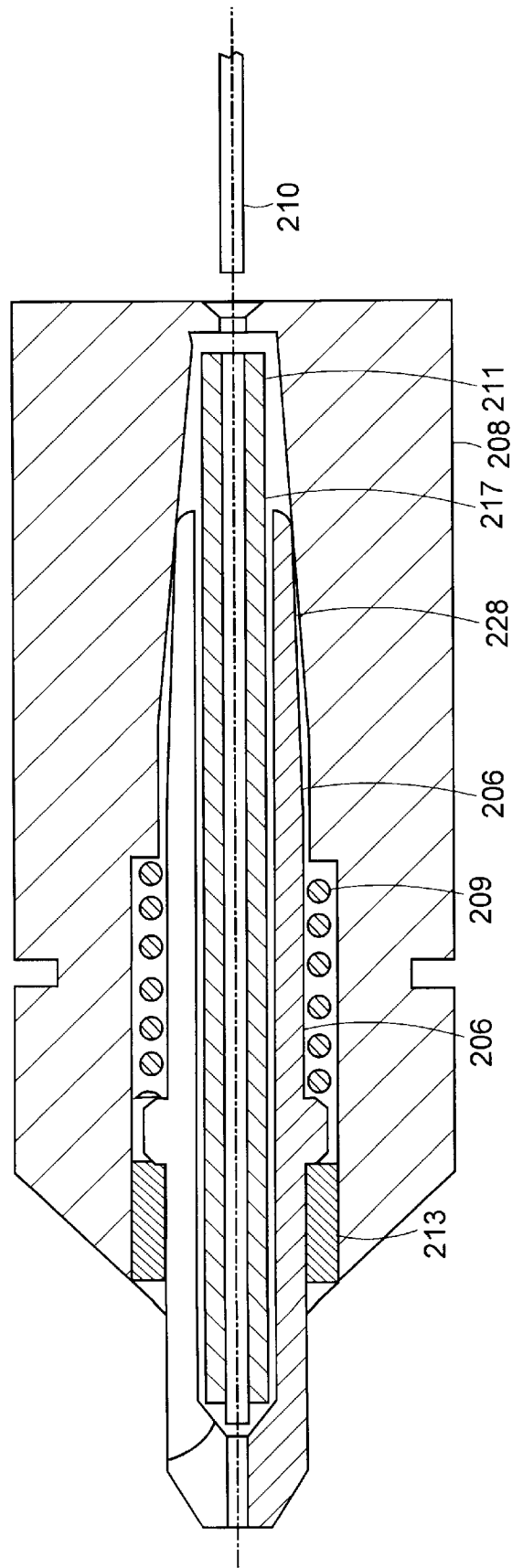

In FIG. 14A the rotary connector is engaged with the motor assembly, and the fingers of rotor ferrule 206 are clamped onto centering and gripping tube 217, due to the internal taper of vee-shaped coupling 208. In FIG. 14B, the rotary connector has been dis-engaged from the motor assembly, and the fingers of rotor ferrule 206 are open, thereby making it possible to remove the guidewire from the rotor ferrule as shown in FIG. 14C. After the guidewire has been removed from the rotor ferrule, a catheter such as the balloon catheter 226 shown in FIG. 14D can be inserted over the proximal end of the guidewire.

FIGS. 15 and 16 show an alternative embodiment in which the rotor assembly is a hand-held connector 333 having a manually rotatable rotor shaft 305. Stator optical fiber 301 is supported by strain relief 330, which is attached to proximal end cap 335 of hand-held connector 333. End cap 335 is fixedly joined to stator ferrule 319, which holds stator optical fiber 301 (and optionally a stator GRIN rod lens at the distal end of fiber 301) in a rotationally stationary position. End cap 335 includes two cutouts 331 on opposite sides of end cap 335 to allow finger access to knurled portion 332 of rotor shaft 305. Rotor shaft 305 is held concentrically within hand-held connector 333 by bearings 308. A sterile barrier 311 automatically interlocks with hand-held connec-tor 333 in the manner described above in connection with FIG. 4. Rotor optical fiber 313 is contained within rotary driveshaft 334, which is housed in sheath or catheter 312 (for purposes of visual clarity the distal ends of catheter sheath 312 and rotatable driveshaft 334 are shown cut away in FIG. 15). Driveshaft 334 ensures uniform rotation at the distal tip of rotor fiber 313. This hand-rotated embodiment can include a single rotatable GRIN rod lens as described above in connection with FIGS. 13 and 14A–14D.

There has been described new and useful connectors for connecting a rotatable optical fiber to a rotor shaft while maintaining the rotatable optical fiber in axial alignment with a stationary optical fiber. It will be apparent to those skilled in the art that numerous modifications of and departures from the specific embodiments described herein are possible without departing from the inventive concepts.

What is claimed is:

1. A connection system comprising:
   a rotatable optical fiber;
   an assembly comprising a conduit for conveying a light beam to the rotatable fiber; and
   a coupling having a rotatable portion attachable to a proximal end of the rotatable fiber, and a stationary portion attachable to the assembly comprising the light beam conduit so as to permit the rotatable fiber to rotate while its proximal end remains in axial alignment with the light beam, the rotatable fiber being disengageable from the rotatable portion when the stationary portion does not engage the assembly comprising the light beam conduit.

2. The connection system of claim 1 wherein the rotatable fiber is non-disengageable from the rotatable portion when the stationary portion engages the assembly comprising the light beam conduit.

3. The connection system of claim 1 wherein the rotatable portion comprising a ferrule with which the rotatable portion attaches to the proximal end of the rotatable fiber.

4. The connection system of claim 3 wherein the ferrule attaches to the proximal end of the rotatable fiber by collet closing action when the stationary portion of the coupling engages the assembly comprising the light beam conduit.

5. The connection system of claim 3 further comprising a spring positioned within the rotatable portion of the coupling that forces the ferrule toward the rotatable stator.

6. The connection system of claim 5 wherein the spring is compressed when the stationary portion of the coupling engages the assembly comprising the light beam conduit.

7. The connection system of claim 1 further comprising a sleeve surrounding the rotatable fiber, the sleeve and the optical fiber forming an optical guidewire.

8. The connection system of claim 7 wherein the sleeve is rotatable with the rotatable fiber.

9. A connection system comprising:
   a rotatable optical fiber;
   a sheath surrounding the rotatable fiber
   an assembly comprising a conduit for conveying a light beam to the rotatable fiber;
   a coupling having a rotatable portion attachable to a proximal end of the rotatable fiber, and a stationary portion attachable to the sheath and the assembly comprising the light beam conduit so as to permit the rotatable fiber to rotate while its proximal end remains in axial alignment with the light beam; and
   a fluid port connected to the stationary portion that enables introduction of fluid into the sheath and around the rotatable optical fiber.

10. The connection system of claim 9 further comprising a fluid port sidearm connected to the fluid port.

11. The connection system of claim 9 further comprising a seal located between the rotatable and stationary portions of the coupling that substantially prevents the fluid from passing toward the assembly comprising the light beam conduit.

12. A connection system comprising:

a rotatable optical fiber;

an assembly comprising a rotor, a fixed housing, and a conduit for conveying a light beam to the rotatable fiber;

a coupling comprising a stationary portion and a rotatable portion, the stationary portion being attachable to the fixed housing, the rotatable portion being attachable to a proximal end of the rotatable optical fiber and to the rotor so as to permit the rotatable fiber to rotate with the rotor while the rotatable fiber remains in axial alignment with the light beam;

the rotor being at least partially hollow and comprising a bearing that holds the light beam conduit in axial alignment with the rotatable fiber when the rotatable portion of the coupling engages the rotor.

13. The connection system of claim 12 wherein the light beam conduit comprises a stationary optical fiber having a distal end portion positioned within the hollow rotor shaft.

14. The connection system of claim 1 wherein the coupling further comprises a lens assembly coupled to a proximal end of the rotatable fiber.

15. The connection system of claim 14 wherein the conduit comprises a stationary fiber, and the lens assembly comprises a rotatable rod lens axially aligned with the proximal end of the rotatable fiber and a stationary rod lens axially aligned with a distal end of the stationary fiber.

16. The connection system of claim 9 wherein the coupling further comprises a lens assembly coupled to a proximal end of the rotatable fiber.

17. The connection system of claim 16 wherein the conduit comprises a stationary fiber, and the lens assembly comprises a rotatable rod lens axially aligned with the proximal end of the rotatable fiber and a stationary rod lens axially aligned with a distal end of the stationary fiber.

18. The connection system of claim 12 wherein the coupling further comprises a lens assembly coupled to a proximal end of the rotatable fiber.

19. The connection system of claim 18 wherein the conduit comprises a stationary fiber, and the lens assembly comprises a rotatable rod lens axially aligned with the proximal end of the rotatable fiber and a stationary rod lens axially aligned with a distal end of the stationary fiber.

* * * * *